United States Patent [19]

Otsuka et al.

[11] Patent Number: 4,971,985
[45] Date of Patent: Nov. 20, 1990

[54] PYRIDYLKETOXIME ETHER COMPOUND AND PHARMACEUTICAL COMPOSITION CONTAINING IT

[75] Inventors: Katsuyuki Otsuka; Nobuo Ishiyama; Makoto Watanabe; Kenji Seri; Kazuko Sanai; Kanji Muraoka, all of Tokyo, Japan

[73] Assignee: Kaken Pharmaceutical Co., Ltd., Tokyo, Japan

[21] Appl. No.: 424,129

[22] Filed: Oct. 19, 1989

[30] Foreign Application Priority Data

Oct. 24, 1988 [JP] Japan .................. 63-267893

[51] Int. Cl.$^5$ ............ A61K 31/44; C07D 213/54
[52] U.S. Cl. .................... 514/357; 514/323; 514/332; 514/336; 514/338; 546/236; 546/264; 546/270; 546/283; 546/284; 546/334
[58] Field of Search .......... 546/264, 270, 284, 334, 546/256, 283; 514/332, 336, 338, 357, 333

[56] References Cited

U.S. PATENT DOCUMENTS

| | | | |
|---|---|---|---|
| 4,297,359 | 10/1981 | van Zorge | 546/283 |
| 4,352,804 | 10/1982 | van Zorge | 514/252 |

FOREIGN PATENT DOCUMENTS

| | | | |
|---|---|---|---|
| 0221601 | 5/1987 | European Pat. Off. | 546/252 |
| 2117772 | 10/1983 | United Kingdom | 546/252 |

OTHER PUBLICATIONS

Chemical Abstracts, vol. 90, No. 13, Mar. 1979, U.S.A., Tankaka et al., Abstract No. 103840m.
Chemical Abstracts, vol. 111, No. 9, Abstract 70,646z. Aug. 28, 1989, p. 51.

*Primary Examiner*—Mary C. Lee
*Assistant Examiner*—Zinna Northington-Davis
*Attorney, Agent, or Firm*—Oblon, Spivak, McClelland, Maier & Neustadt

[57] ABSTRACT

A pyridylketoxime ether compound of the formula:

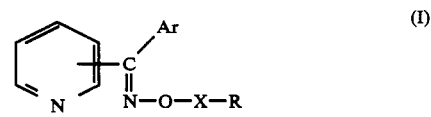

wherein Ar is a phenyl, naphthyl, or heterocyclic group unsubstituted or substituted by a $C_1$-$C_8$ alkyl group, a $C_1$-$C_8$ alkylamino group, a $C_1$-$C_8$ alkoxy group, a $C_1$-$C_8$ alkoxycarbonyl group, a trifluoromethyl group, a nitro group or a halogen atom, X is a —$(CH_2)_m$— group wherein m is an integer of from 1 to 5, a —$(CH_2)_m$—Y— group wherein Y is an oxygen or sulfur atom and m is as defined above, or a —$CH_2$—$(CH=CH)_n$— group wherein n is an integer of 1 or 2, and R is a phenyl, naphthyl, $C_3$-$C_8$ cycloalkyl or heterocyclic group unsubstituted or substituted by a $C_1$-$C_8$ alkyl group, a $C_1$-$C_8$ alkylamino group, a $C_1$-$C_8$ alkoxy group, a $C_1$-$C_8$ akloxycarbonyl group, a trifluoromethyl group, a nitro group or a halogen atom, or a salt thereof.

6 Claims, No Drawings

PYRIDYLKETOXIME ETHER COMPOUND AND PHARMACEUTICAL COMPOSITION CONTAINING IT

The present invention relates to novel pyridylketoxime compounds and pharmaceutical compositions containing them.

In recent years, as the old aged population has increased, various ischemic diseases which cause serious health troubles and various cerebral diseases, heart diseases and pheripheral circulatory failures related thereto, such as myocardial infarction, angina pectoris, cerbral apoplexy, cerebral thrombosis and cerebral infarction, have increased.

At present, a calcium antagonistic agent, particularly, a calcium channel blocking agent, is clinically widely used as one of curing agents of these diseases. In future, however, it is desired to develop a drug having a calmodulin antagonism as a calcium antagonistic agent having a better functional mechanism.

On the other hand, it has been reported that various ketoxime ether derivaties are useful as drugs. Namely, e.g. U.S. Pat. No. 4,352,804 discloses pyradinylketoxime ether derivatives, and U.S. Pat. No. 4,297,359 discloses ketoxime alkyl ether derivatives. However, these derivaties are all disclosed to be used for the treatment of the gastroenteric tract, and no study has been made for their application to the treatment of ischemic diseases or various diseases related thereto.

Accordingly, a first object of the present invention is to provide a novel compound having a calmodulin antagonism and being useful for the treatment of ischemic diseases and various diseases related thereto.

A second object of the present invention is to provide a pharmaceutical composition containing such a novel compound as an active ingredient.

The present inventors have synthesized novel pyridylketoxime ether compounds and studied their calmodulin antagonism. As a result, it has been found that these compounds have not only a calmodulin antagonism but also a calcium channel antagonism and an activity to improve the deformation of erythrocytes, and as such they are very useful as curing agents for ischemic diseases. The above objects have been accomplished on the basis of this discovery.

The present invention provides a pyridylketoxime ether compound of the formula:

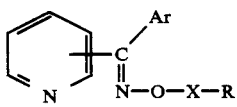 (I)

wherein Ar is a phenyl, naphthyl or heterocyclic group unsubstituted or substituted by a $C_1$-$C_8$ alkyl group, a $C_1$-$C_8$ alkylamino group, a $C_1$-$C_8$ alkoxy group, a $C_1$-$C_8$ alkoxycarbonyl group, a trifluoromethyl group, a nitro group or a halogen atom, X is a —$(CH_2)_m$- group wherein m is an integer of from 1 to 5, a —$(CH_2)_m$-Y- group wherein Y is an oxygen or sulfur atom and m is as defined above, or a —$CH_2$—$(CH=CH)_n$- group wherein n is an integer of 1 or 2, and R iS a phenyl, naphthyl, $C_3$-$C_8$ cycloalkyl or heterocyclic group unsubstituted or substituted by a $C_1$-$C_8$ alkyl group, a $C_1$-$C_8$ alkylamino group, a $C_1$-$C_8$ alkoxy group, a $C_1$-$C_8$ alkoxycarbOnyl group, a trifluoromethyl group, a nitro group or a halogen atom, or a salt thereof.

The present invention also provides a pharmaceutical composition comprising an effective amount of the compound of the formula I or its salt, as the active ingredient, and a pharmaceutical carrier or diluent and having a calmodulin antagonism.

Now, the present invention will be descirbed in detail with reference to the preferred embodiments.

Firstly, the pyridylketoxime ether compounds of the present invention will be described.

The pyridylketoxime ether compounds of the formula I are novel compounds which are distinguished from the compounds disclosed in the above-mentioned U.S. Pat. Nos. 4,352,804 and 4,297,359 in respect of the following structural diferences (a) and (b).

(a) The pyridylketoxime ether compounds of the formula I of the present invention have a pyridyl group as an essential substituent. Whereas, the compounds disclosed in U.S. Patent 4,352,804 have, instead of the pyridyl group, a heterocyclic group containing two hetero atoms, at least one of which is a nitrogen atom.

(b) The pyridylketoxime ether compounds of the formula I of the present invention are different from the compounds disclosed in U.S. Pat. Nos. 4,352,804 and 4,297,359 in the substitutent bonded to the oxygen atom of the ketoxime ether group.

In the formula I representing the pyridylketoxime ether compounds of the present invention, the aromatic ring for Ar and R is preferably a phenyl group or a naphthyl group, and the heterocyclic group is preferably a single ring or condensed ring heterocyclic group having from 1 to 3 nitrogen, oxygen or sulfur atoms as hetero atoms, more preferably a single ring heterocyclic group containing one nitrogen, oxygen or sulfur atom as a hetero atom or a condensed ring heterocyclic group containing two oxygen atoms as hetero atoms, As a single heterocyclic group containing one nitrogen, oxygen or sulfur atom as a hetero atom, a furyl group, a thienyl group or a pyridyl group is, for example, preferred. Likewise, as a condensed ring heterocyclic group containing two oxygen atoms as hetero atoms, a 1,3-dioxaindanyl group is, for example, preferred.

In the formula I, the cycloalkyl group for R is preferably a cycloalkyl group having from 3 to 8 carbon atoms such as a cyclopropyl group, a cyclobutyl group, a cyclopentyl group, acyclohexyl group, a cycloheptyl group or a cyclooctyl group.

In the formula I, the phenyl group, the naphthyl group and the heterocyclic group for Ar or the phenyl group, the naphthyl group, the cycloalkyl group and the heterocyclic group for R may be substituted preferably by one or two substitutents. Such substitutents may be an alkyl group having from 1 to 8 carbon atoms, an alkylamino group having from 1 to 8 carbon atoms, an alkoxy group having from 1 to 8 carbon atoms, an alkoxycarbnyl group having from 1 to 8 carbon atoms, a trifluoromethyl group, a nitro group or a halogen atom.

The alkyl group having from 1 to 8 carbon atoms may be a straight chain or branched alkyl group such as a methyl group, an ethyl group, a n-propyl group, an isopropyl group, a nbutyl group, a s-butyl group, a t-butyl group, a n-pentyl group, a n-hexyl group, a n-heptyl group or a n-octyl group. The alkylamino group having from 1 to 8 carbon atoms may preferably be, for example, a methylamino group, a dimethylamino group, an ethylamino group, a diethylamino group, a n-propylamino group, an isopropylamino group, a n- butylamino group, a s-butylamino group, a t butylamino group, a n-pentylamino group, a n-hexylamino group, a n-heptylamino group or a n-octylamino group. The alkoxy group having from 1 to 8 carbon atoms may preferably be, for example, a methoxy group, an ethoxy group, a n-propoxy group, an isopropoxy group, a n-butoxy group, a s-butoxy group, a t-butoxy group, a n-pentoxy group, a n-hexoxy group, a n-heptoxy group or a n-octoxy group. The alkoxycarbonyl group having from 1 to 8 carbon atoms may preferably be, for example, a methoxy carbonyl group, an ethoxycarbonyl group, a n-propoxycarbonyl group, an isopropoxycarbonyl group, a n-butoxycarbonyl group, a s-butoxycarbonyl group, a t-butoxycarbonyl group, a n pentoxycarbonyl group, a n-hexoxycarbonyl group, a n-heptoxycarbonyl group or a n-octoxycarbonyl group.

The halogen atom is preferably, for example, a fluorine atom, a chlorine atom or a bromine atom.

The pyridylketoxime ether compounds of the present invention may be salts. As such salts, acid addition salts may be mentioned. Such acid addition salts can readily be obtained by reacting the pyridylketoxime ether compounds with inorganic acids or organic acids. Such inorganic acids include, for example, hydrochloric acid, hydrobromic acid, hydroiodic acid and sulfuric acid. The organic acids include, for example, maleic acid, fumaric acid, succinic acid, acetic acid, malonic acid, a citric acid, benzoic acid, oxalic acid and methane sulfonic For the production of the pyridylketoxime compounds of the formula I of the present invention, the following processes are preferably employed.

(1) Production process (a)

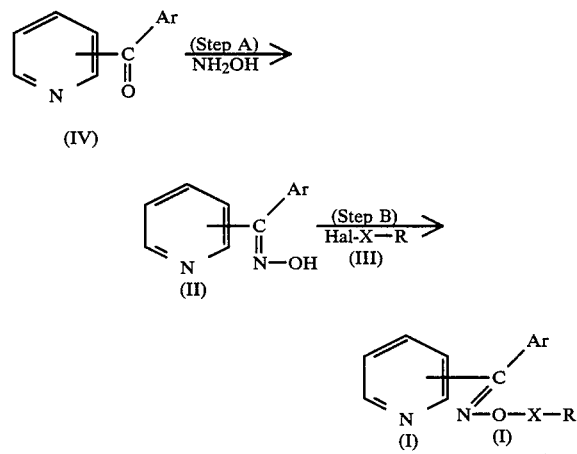

In the above formulas, Ar, X and R are as defined above, and Hal is a halogen atom.

Namely, a pyridylketone of the formula IV is reacted with hydroxylamine to obtain a pyridylketoxime of the formula II (Step A).

Then, a halide of the formula III is reacted thereto for a condensation reaction to obtain a compound of the formula I as the desired substance (Step B). Further, if necessary, this product is converted to its salt.

In Step A, the reaction temperature is usually from about 0° to 200° C., preferably from room temperature to 100° C. As the solvent, methanol, ethanol, propanol, benzene, toluene or water may, for example, be employed.

In Step B, the reaction temperature is usually from about 0° to 100° C. As the solvent, dimethylformamide (DMF), dimethylsulfoxide (DMSO), methanol, ethanol, propanol, benzene or toluene may, for example, be used. In this case, particularly good results can be obtained by conducting the reaction in the presence of a base such as sodium hydride (NaH), triethylamine, dimethylaniline, potassium hydroxide, sodium methoxide, sodium ethoxide or potassium t-butoxide.

(2) Production process (b)

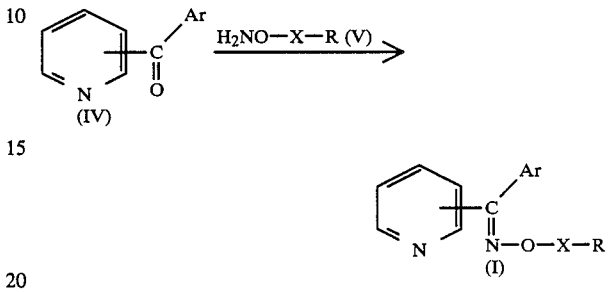

In the above formula, Ar, X and R are as defined above.

To the compound of the formula IV, an 0-substituted hydroxylamine derivative of the formula V is reacted for condensation to obtain the desired compound of the formula I'. In this process (b), the reaction temperature is usually from about 0 to 200° C, and as the solvent, methanol, ethanol, propanol, benzene, toluene or water may, for example, be used.

Now, the representative examples of the pyridiylketoxime ether compound of the formula I of the present invention will be given. However, these examples are presented to facilitate the understanding of the present invention, and it should be understood that the present invention is by no means restricted by such specific examples.

O-benzyl-phenyl-2-pyridylketoxime,
O-benzyl-phenyl-3-pyridylketoxime,
O-benzyl-phenyl-4-pyridylketoxime,
O-(4-methylbenzyl)-phenyl-2-pyridylketoxime,
O-(4-methylbenzyl)-phenyl-3-pyridylketoxime,
O-(4-methylbenzyl)phenyl-4-pyridylketoxime,
O-(4 chlorobenzyl)-phenyl-2-pyridylketoxime,
O-(4-chlorobenzyl)-phenyl-3-pyridylketoxime,
O-(4-chlorobenzyl)-phenyl-4-pyridylketoxime,
O-(3,4-dimethoxybenzyl)-phenyl-2-pyridylketoxime,
O-(3,4-dimethoxybenzyl)-phenyl-3-pyridiylketoxime,
O-(3,4-dimethoxybenzyl)-phenyl-4-pyridylketoxime,
O-(2-pyridylmethyl)-phenyl-2-pyridylketoxime,
O-(2-pyridylmethyl)-phenyl-3-pyridylketoxime,
O-(2-pyridylmethyl)-phenyl-4-pyridylketoxime,
O-(1-naphthylmethyl)-phenyl-2-pyridylketoxime,
O-(1-naphthylmethyl)-phenyl-3-pyridylketoxime,
O-(1-naphthylmethyl)-phenyl-4-pyridylketoxime,
O-(2-thienylmethyl)-phenyl-2-pyridylketoxime,
O-(2-thienylmethyl)-phenyl-3-pyridylketoxime,
O-(2-thienylmethyl)-phenyl-4-pyridylketoxime,
O-cinnamyl-phenyl-2-pyridylketoxime,
O-cinnamyl-phenyl-3-pyridylketoxime,
O-cinnamyl-phenyl-4-pyridylketoxime,
O-[2-(2-methylphenyl)ethyl]-phenyl-3-pyridylketoxime,
O-[2-(3-methylphenyl)ethyl]-phenyl-3-pyridylketoxime,
O-[2-(4-methylphenyl)ethyl]-phenyl 3-pyridylketoxime,
O-[2-(2 methoxyphenyl)ethyl]-phenyl 3-pyridylketoxime, O-[2-(3-methoxyphenyl)ethyl]-phenyl-3-pyridylketoxime,
O-[2-(4-methoxyphenyl)ethyl]-phenyl-3-pyridylketoxime,
O-[2-(2,5-dimethoxyphenyl)ethyl]-phenyl-3-pyridylketoxime,
O-[2-(3,4-dimethoxyphenyl)ethyl]-phenyl-3-pyridylketoxime,
O-[2-(2,6-dimethoxyphenyl)ethyl]-phenyl-3-pyridylketoxime,
O-O-[2-(2-thienyl)ethyl]-phenyl-3-pyridylketoxime,
O-O-[2-(3-thienyl)ethyl]-phenyl-3-pyridylketoxime,
O-O-[2-(1-naphthyl)ethyl]-phenyl-3-pyridylketoxime,
O-[2-furyl)ethyl]-phenyl-3-pyridylketoxime,
O-[2-(3-pyridyl)ethyl]-phenyl-3-pyridylketoxime,
O-(2-cyclohexylethyl)-phenyl-3-pyridylketoxime,
O-(3-phenylpropyl)-phenyl-3-pyridylketoxime,
O-(4-phenylbutyl)-phenyl-3-pyridylketoxime,
O-(5-phenylpentyl)-phenyl-3-pyridylketoxime,
O-(2-phenylethyl)-o-tolyl-3-pyridylketoxime,
O-(2-phenylethyl)-m-tolyl-3-pyridylketoxime,
O-(2-phenylethyl)-p-tolyl-3-pyridylketoxime,
O-(2-phenylethyl) 2,4-dimethoxyphenyl-3-pyridylketoxime,
O-(2-phenylethyl)-2,5-dimethoxyphenyl-3-pyridylketoxime,
O-(2-phenylethyl)-3,4-dimethoxyphenyl-3-pyridylketoxime,
O-(2-phenylethyl)-2-chlorophenyl-3-pyridylketoxime,
O-(2 phenylethyl)-3-chlorophenyl-3-pyridylketoxime,
O-(2 phenylethyl)-3-fluorophenyl-3-pyridylketoxime,
O-(2-phenylethyl)-3-trifluoromethylphenyl-3-pyridylketoxime,
O-(2-phenylethyl)-3-nitrophenyl-3-pyridylketoxime,
O-(2-phenylethyl-2,5-xylyl-3-pyridylketoxime,
O-(2-phenylethyl)-2-thienyl-3-pyridylketoxime,
O-(2-phenylethyl)-2-furyl-3-pyridylketoxime,
O-(2-phenylethyl)-4-N,N-dimethylaminophenyl-3-pyridylketoxime,
O-(2-phenylethyl) 1-naphthyl-3-pyridylketoxime,
O-(2-phenylethyl)-3,4-methylenedioxyphenyl-3-pyridylketoxime,
O-(2-phenylethyl)-bis-(3-pyridyl)ketoxime,
O-[(2-phenylthio)ethyl]-phenyl-3-pyridylketoxime,
O-[(2-phenoxy)ethyl]-phenyl-2-pyridylketoxime,
O-[(2-phenoxy)ethyl]-phenyl-3-pyridylketoxime,
O-[(2-phenoxy)ethyl]-phenyl-4-pyridylketoxime,
O-[2-(4-methoxyphenoxy)ethyl]-phenyl-3-pyridylketoxime,
O-[2-(4-methoxyphenoxy)ethyl]-phenyl-2-pyridylketoxime,
O-[2-(4-methoxyphenoxy)ethyl]-phenyl-4-pyridylketoxime,
O-[2-(4-chlorophenoxy)ethyl]-phenyl-2-pyridylketoxime,
O-[2-(4-chlorophenoxy)ethyl]-phenyl-3-pyridylketoxime,
O-[2-(4-chlorophenoxy)ethyl]-phenyl-4-pyridylketoxime,
O-[2-(3-trifluoromethylphenoxy)ethyl]-phenyl-2-pyridylketoxime,
O-[2-(3-trifluoromethylphenoxy)ethyl]-phenyl-3-pyridylketoxime,
O-[2-(3-trifluoromethylphenoxy)ethyl]-phenyl-4-pyridylketoxime,
O-[2-(4-methoxyphenyl)ethyl]-3,4-dimethoxyphenyl-4-pyridylketoxime,
O-[2-(3,4-dimethoxyphenyl)ethyl]-3,4-dimethoxyphenyl-4-pyridylketoxime,
O-[2-thienylethyl]3,4 dimethoxyphenyl-4-pyridylketoxime,
O-[2-(3,4-dimethoxyphenyl)ethyl]-3-nitrophenyl-4-pyridylketoxime,
O-[2-(4-chlorophenyl)ethyl]-3,4-dimethoxyphenyl-4-pyridylketoxime, and
O-[2-(3,4-dimethoxyphenyl)ethyl]-bis-(3-pyridyl)ketoxime.

Now, the pharmaceutical composition of the present invention will be described.

The pyridylketoxime ether compounds of the present invention are found to have not only an excellent calmodulin antagonism but also a $Ca^{2+}$ channel antagonism and an acitivity to improve the deformation of erythrocytes. Accordingly, the pharmaceutical compositions of the present invention containing such pyridylketoxime ether compounds as active ingredients, are useful as curing agents based on these activities, for example, as curing agents for isochemic diseases or vasodilators. Specifically, they are useful for curing or preventing cerebral vessel troubles such as ephemeral cerebral ischemic attack, cerebral infarction and encephalo-arteriosclerosis, or ischemic heart troubles such as angina pectoris and myocardial infarction. Further, they are useful for the prevention of the recurrence of these diseases or for improvement after the treatment.

The pharmaceutical compostion of the present invention may be constituted solely by the pyridylketoxime ether compound of the formula I and/or its salt. However, it is usually preferred to formulate it with a suitable carrier into a drug formulation for oral or non-oral administration. As formulations for oral administration, tablets, capsules and granules may be mentioned. As formulations for non-oral administration, intravenous, intramuscular or subcutaneous injection drugs, or suppositories may be mentioned. These formulations can be prepared readily in accordance with conventional methods.

The dose of the pyridylketoxime ether compound of the present invention varies depending upon the administration route, the type of formulation, the diseased condition of the patient, etc., but is usually within a range of from 0.01 to 100 mg/kg of the body weight, preferably from 0.1 to 10 mg/kg of the body weight.

Now, the present invention will be described in further detail with reference to Examples and Test Examples. However, it should be understood that the present invention is by no means restricted by such specific Examples.

EXAMPLE 1

Preparation of
O-(2-phenylethyl)-phenyl-3-pyridylketoxime
(Compound No. 1)

1.06 g (0.016 mol) of potassium hydroxide was dissolved in 80 ml of ethanol, and 3.17 g (0.016 mol) of phenyl-3-pyridylketoxime was added thereto and dissolved under stirring. To this solution, 2.96 g (0.016 mol) of β-phenylethylbromide was added, and the mixture was stirred at room temperature for two hours. Then, it was stirred and reacted at 80° C. Four hours later, the reaction solution was distilled under reduced pressure to remove ethanol. Then, 100 ml of a 3N sodium hydroxide aqueous solution was added to the residue, and the mixture was extracted with benzene.

The extract solution was washed with a 3N sodium hydroxide aqueous solution and water and dried over anhydrous sodium sulfate. Then, benzene was distilled off under reduced pressure. The residual oily substance was purified by silica gel chromatography to obtain 2.6 g of the above-identified compound as an oily substance.

NMR(CDCl$_3$)δ:2.96(t,2H), 4.40(t,2H), 6.80–7.76(m, 12H), 8.32–8.72(m,2)

EXAMPLE 2

Preparation of O-(2-phenylethyl)-3,4-dimethoxyphenyl-3-pyridylketoxime (Compound No. 56)

3.48 g (0.015 mol) of 3,4-dimethoxyphenyl-3pyridylketone was dissolved in 80 ml of ethanol, and 2.7 g (0.015 mol) of o-phenethylhydroxylamine hydrochloride was added thereto. The mixture was stirred and reacted at room temperature. Ten hours later, the reaction solution was distilled under reduced pressure to remove ethanol. A 2N sodium hydroxide aqueous solution was added to the reaction solution, and the mixture was extracted with benzene. The extract solution was washed with water and dried over anhydrous sodium sulfate. Benzene was distilled off, and the residual oily substance was purified by silica gel chromatography to obtain 2.3 g of the above-identified compound.

NMR(CDCl$_3$)δ:2.83(t), 3.00(t)(2H), 3.67(s,3H), 3.77(s,3H), 4.36(t), 4.43(t)(2H), 6.67–7.86(m,10H), 8.50–8.80(m,2H)

The compounds identified in the following Table were obtained in a manner similar to Examples 1 and 2.

| Compound No. | (pyridyl) | Ar | —X—R | Physical properties | NMR (CDCl$_3$)δ: |
|---|---|---|---|---|---|
| 1 | 3-pyridyl | phenyl | —CH$_2$CH$_2$—phenyl | Oily | 2.96(t, 2H), 4.40(t, 2H) 6.80–7.76(m, 12H), 8.32–8.72(m, 2H) |
| 2 | 2-pyridyl | " | " | " | 2.60–3.20(m, 2H), 4.00–4.60(m, 2H), 7.0–7.9(m, 13H), 8.56(m, 1H) |
| 3 | 4-pyridyl | " | " | " | 3.00(t, 2H), 4.42(t, 2H) 7.23, 7.40(m, 12H), 8.63(m, 2H) |
| 4 | 2-pyridyl | " | —CH$_2$—phenyl | " | 5.12(s), 5.25(s)(2H), 6.95–7.70(m, 13H), 8.50(d), 8.55 (d)(1H). |
| 5 | 3-pyridyl | " | " | " | 5.23(s, 2H), 7.0–8.0(m, 12H), 8.5–8.8(m, 2H). |
| 6 | 4-pyridyl | " | " | " | 5.21(s), 5.25(s)(2H), 7.34, 7.42 (m, 12H), 8.63(d), 8.77(d)(2H). |
| 7 | 2-pyridyl | " | —CH$_2$—C$_6$H$_4$—CH$_3$ | Oily | 2.27(s, 3H), 5.15(s)5.21(s)(2H), 6.97–7.85(m, 12H), 8.56(d)8.66(d 1H). |
| 8 | 3-pyridyl | " | " | " | 2.33(s, 3H), 5.20(s, 2H), 7.0–8.0 (m, 11H), 8.5–8.8(m, 2H). |

-continued
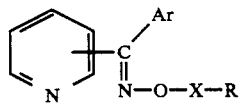
(I)
| Compound No. | ⟨N⟩ | Ar | —X—R | Physical properties | NMR (CDCl₃)δ: |
|---|---|---|---|---|---|
| 9 | 4-pyridyl | " | " | m.p. 44–47° C. | 2.34(s, 3H), 5.18(s)5.22(s)(2H), 7.18–7.38(m, 11H), 8.54(d), 8.67 (d)(2H). |
| 10 | 2-pyridyl | " | —CH₂—C₆H₄—Cl | m.p. 98–100° C. | 5.12(s)5.15(s)(2H), 6.88–7.69 (m, 12H), 8.53(t, 1H). |
| 11 | 3-pyridyl | " | " | m.p. 53–54° C. | 5.2(s, 2H), 7.0–8.0(m, 11H), 8.5–8.8(m, 2H). |
| 12 | 4-pyridyl | " | " | Oily | 5.21(s)5.25(s)(2H), 7.34, 7.42 (m, 11H), 8.63(d)8.77(d)(2H). |
| 13 | 2-pyridyl | " | —CH₂—C₆H₃(OCH₃)₂ | Oily | 3.82(s, 6H), 5.15(s)5.18(s)(2H), 6.53–6.77(m, 3H), 7.0–7.85(m, 8 H), 8.63(t, 1H). |
| 14 | 3-pyridyl | " | " | " | 3.86(s, 6H), 5.2(s, 2H), 6.89(s, 3 H), 7.2–8.0(m, 7H), 8.5–8.8(m, 2H). |
| 15 | 4-pyridyl | " | " | " | 3.81(s, 3H), 3.83(s, 3H), 5.12(s) 5.15(s)(2H), 6.82(s, 3H), 7.30 (m, 7H), 8.52(m, 2H). |
| 16 | 2-pyridyl | " | —CH₂—(2-pyridyl) | Oily | 5.39(S)5.45(s)(2H), 6.97–7.97 (m, 11H), 8.56(t, 1H), 8.69(t, 1H). |
| 17 | 3-pyridyl | " | " | " | 5.4(s, 2H), 7.0–8.0(m, 10H), 8.5–8.8(m, 3H). |
| 18 | 4-pyridyl | " | " | " | 5.36(s)5.40(s)(2H), 7.34(m, 8H), 7.68(m, 1H), 8.68(d, 2H), 8.74(d, 1H). |

-continued
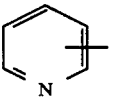
(I)
| Compound No. | 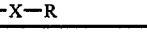 | Ar | —X—R | Physical properties | NMR (CDCl₃)δ: |
|---|---|---|---|---|---|
| 19 |  | 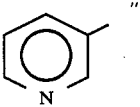 | 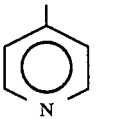 | Oily | 5.60(s)5.66(s)(2H), 6.66–8.33 (m, 15H), 8.50(t, 1H). |
| 20 | 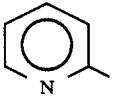 | " | " | m.p. 82–84° C. | 5.76(s, 2H), 6.8–8.0(m, 14H), 8.5–8.8(m, 2H). |
| 21 | 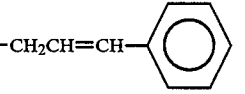 | " | " | Oily | 5.63(s)5.66(s)(2H), 7.10(d, 2H), 7.38(m, 8H), 7.73–8.10(m, 4H) 8.56(m, 2H). |
| 22 | 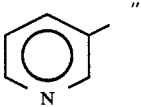 | " | —CH₂CH=CH—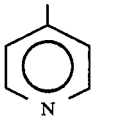 | Oily | 4.88(d, 2H), 6.33–6.69(m, 2H), 6.88–7.85(m, 13H), 8.63(t, 1H). |
| 23 | 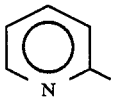 | " | " | Oily | 4.58(d, 2H), 6.0–6.6(m, 2H), 7.0–8.0(m, 12H), 8.5–8.8(m, 3H). |
| 24 | 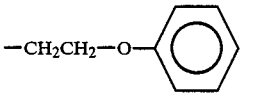 | " | " | m.p. 60–63° C. | 4.83(d)4.86(d)(2H), 6.16–6.82 (m, 2H), 7.28(m, 12H), 8.55(d) 8.69(d)(2H). |
| 25 | 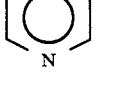 | " | —CH₂CH₂—O—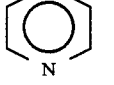 | m.p. 73–77° C. | 4.0–4.33(m, 2H), 4.33–4.66(m, 2H), 6.69–7.85(m, 13H), 8.56(t, 1H). |
| 26 | 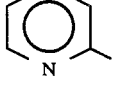 | " | " | m.p. 47–49° C. | 4.30(t, 2H), 4.56(t, 2H), 6.8–8.0(m, 12H), 8.5–8.8(m, 2H). |
| 27 | 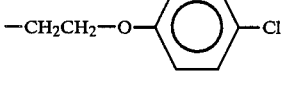 | " | " | Oily | 4.26(m, 2H), 4.50(m, 2H), 6.84(d, 2H), 7.24(m, 10H), 8.52(d)8.61(d)(2H). |
| 28 | | " | —CH₂CH₂—O—〈⎯〉—Cl | m.p. 80–84° C. | 4.0–4.33(m, 2H), 4.33–4.66(m, 2H), 6.69–6.97(m, 2H), 7.0–7.85(m, 8H), 8.66(t, 1H). |

-continued $$\text{(I)}$$

| Compound No. | Ar | —X—R | Physical properties | NMR (CDCl₃)δ: |
|---|---|---|---|---|
| 29 | 3-pyridyl | " | m.p. 64–67° C. | 4.20(t, 2H), 4.50(t, 2H), 6.83 (d, 2H), 7.24(d, 2H), 7.2–7.9 (m, 7H), 8.5–8.8(m, 2H). |
| 30 | 4-pyridyl | " | Oily | 4.20(t, 2H), 4.56(t, 2H), 6.83 (d, 2H), 7.24(d, 2H), 7.2–7.9 (m, 7H), 8.5–8.8(m, 2H). |
| 31 | 2-pyridyl | —CH₂CH₂—O—C₆H₄—OCH₃ | m.p. 71–74° C. | 3.66(s, 3H), 4.0–4.33(m, 2H), 4.33–4.66(m, 2H), 6.82(s, 4H), 7.0–7.85(m, 8H), 8.60(t, 1H). |
| 32 | 3-pyridyl | " | Oily | 3.72(s, 3H), 4.20(t, 2H), 4.50 (t, 2H), 6.82(s, 4H), 7.2–7.9 (m, 7H), 8.5–8.8(m, 2H). |
| 33 | 4-pyridyl | phenyl | —CH₂CH₂—O—C₆H₄—OCH₃ | m.p. 65–66° C. | 3.77(s, 3H), 4.23(m, 2H), 4.53 (m, 2H), 6.87(s, 4H), 7.40(m, 7H) 8.67(m, 2H). |
| 34 | 2-pyridyl | " | —(CH₂)₃—C₆H₅ | Oily | 1.80–2.20(m, 2H), 2.26(t)2.64 (t)(2H), 4.16(t)4.24(t)(2H) 7.0–7.8(m, 13H), 8.55(d)8.67(d)(2H) |
| 35 | 3-pyridyl | " | " | " | 2.00(m, 4H), 2.64(t, 2H), 4.20(t, 2H), 7.16–7.36(m, 11H), 7.70(m, 1H) 8.63(m, 2H) |
| 36 | 4-pyridyl | " | " | " | 2.00(m, 2H), 2.63(t)2.65(t)(2H), 7.0–7.6(m, 12H), 8.54(d) 8.68(d)(2H). |
| 37 | 2-pyridyl | " | —(CH₂)₄—C₆H₅ | " | 1.71(m, 4H), 2.60(t, 2H), 4.18(t) 4.25(t)(2H), 7.15, 7.35(m, 12H), 7.65(m, 1H), 8.57(d)8.67(d)(1H). |
| 38 | 3-pyridyl | " | " | " | 1.73(m, 4H), 2.64(t, 2H), 4.26 (t, 2H), 7.21, 7.39(m, 11H), 7.70 (m, 1H), 8.63(m, 2H). |
| 39 | 4-pyridyl | " | " | " | 1.70(m, 4H), 2.60(t, 2H), 4.18 (m, 2H), 7.13, 7.32(m, 12H), 8.51(d)8.63(d)(2H). |

-continued $$\text{(I)}$$

Structure: pyridine-C(=N-O-X-R)(Ar)

| Compound No. | Pyridine | Ar | —X—R | Physical properties | NMR (CDCl₃)δ: |
|---|---|---|---|---|---|
| 40 | 2-pyridyl | " | —(CH₂)₃—C₆H₅ | " | 1.71–2.03(m, 6H), 2.60(t, 2H), 4.20 (t)4.25(t)(2H), 7.20, 7.40(m, 12H) 7.70(m, 1H), 8.67(m, 1H). |
| 41 | 3-pyridyl | " | " | " | 1.20–1.86(m, 6H), 2.60(t, 2H), 4.10 (t, 2H), 7.12, 7.28(m, 11H), 7.62(m, 1H), 8.54(m, 2H). |
| 42 | 4-pyridyl | " | " | " | 1.20–1.92(m, 6H), 2.60(t, 2H), 4.20 (t)4.22(t)(2H), 7.25, 7.41(m, 12H) 8.64(d)8.74(d)(2H). |
| 43 | 3-pyridyl | " | —CH₂CH₂—C₆H₄(o-CH₃) | " | 2.30(s, 3H), 3.03(t, 2H), 4.39 (t, 2H), 7.03–7.88(m, 11H), 8.50–8.85(m, 2H). |
| 44 | 3-pyridyl | " | —CH₂CH₂—C₆H₄(m-CH₃) | " | 2.30(s, 3H), 2.94(t, 2H), 4.39 (t, 2H), 6.79–7.88(m, 11H), 8.50–8.85(m, 2H). |
| 45 | 3-pyridyl | C₆H₅ | —CH₂CH₂—C₆H₄—CH₃ | Oily | 2.30(s, 3H), 2.97(t, 2H), 4.36 (t, 2H), 7.03(s, 4H).7.15–7.88 (m, 7H), 8.47–8.82(m, 2H). |
| 46 | 3-pyridyl | " | —CH₂CH₂—C₆H₄(o-Cl) | " | 3.03(t, 2H), 4.50(t, 2H), 7.03–7.97(m, 11H), 8.50–8.85 (m, 2H). |
| 47 | 3-pyridyl | " | —CH₂CH₂—C₆H₄(m-Cl) | " | 2.94(t, 2H), 4.36(t, 2H), 6.85–7.91(m, 11H), 8.50–8.95(m, 2H). |
| 48 | 3-pyridyl | " | —CH₂CH₂—C₆H₄(p-Cl) | " | 3.03(t, 2H), 4.39(t, 2H), 7.00–8.00(m, 11H), 8.56–8.91(m, 2H). |
| 49 | 3-pyridyl | " | —CH₂CH₂—C₆H₄(o-OCH₃) | " | 3.03(t, 2H), 3.79(s, 3H), 4.43(t, 2H), 6.66–7.91(m, 11H), 8.50–8.82(m, 2H). |

-continued $$\text{(I)}$$

Structure: pyridine-C(Ar)=N-O-X-R

| Compound No. | N (pyridine position) | Ar | —X—R | Physical properties | NMR (CDCl₃)δ: |
|---|---|---|---|---|---|
| 50 | 3-pyridyl | " | —CH₂CH₂—(C₆H₄)—OCH₃ (o) | " | 3.00(t, 2H), 3.69(s, 3H), 4.36 (t, 2H), 6.66–7.00(m, 4H), 7.06 –7.91(m, 7H), 8.53–8.95(m, 2H). |
| 51 | 3-pyridyl | " | —CH₂CH₂—(C₆H₄)—OCH₃ (p) | " | 2.94(t, 2H), 3.70(s, 3H), 4.39(t, 2H), 6.66–8.00(m, 11H), 8.50–8.95(m, 2H). |
| 52 | 3-pyridyl | " | —CH₂CH₃—(C₆H₃)(OCH₃)₂ | " | 3.82(s)3.85(s)(6H), 3.00(t, 2H), 4.50(t, 2H), 6.66–7.00(s, 3H), 7.06–7.79(m, 7H), 8.39–8.88(m, 2H). |
| 53 | 3-pyridyl | " | —CH₂CH₂—(2-thienyl) | " | 3.15(t, 2H), 4.36(t, 2H), 6.66–7.74(m, 10H) 8.39–8.88(m,2H). |
| 54 | 3-pyridyl | " | —CH₂CH₂—(3-thienyl) | " | 2.94(t, 2H), 4.30(t, 2H), 6.53–7.74(m, 10H), 8.18–8.69(m, 2H). |
| 55 | 3-pyridyl | " | —CH₂CH₂—cyclohexyl | " | 0.33–2.27(b, 13H), 4.21(t, 2H), 6.94–7.91(m, 7H) 8.36–8.79(m, 2H). |
| 56 | 3-pyridyl | 3,4-dimethoxyphenyl | —CH₂CH₂—C₆H₅ | Oily | 2.93(t), 3.00(t)(2H), 3.67(s, 3H), 3.77(s, 3H), 4.36(t), 4.43(t)(2H), 6.67–7.86(m, 10H), 8.50–8.80(m, 2H) |
| 57 | 3-pyridyl | 4-chlorophenyl | " | " | 3.05(t, 2H), 4.48(t, 2H), 7.1–7.6 (m, 10H), 7.6–8.0(m, 1H) 8.5–8.8(m, 2H) |
| 58 | 3-pyridyl | 2-chlorophenyl | " | " | 3.37(t)3.40(t)(2H), 4.73(t) 4.78(t)(2H), 7.0–8.0(m, 11H), 8.4–8.9(m, 2H). |
| 59 | 3-pyridyl | 2,5-dimethoxyphenyl | " | " | 2.96, 3.00(t, 2H), 3.36, 3.40(t, 2H) 3.40, 3.56, 3.80, 3.85(s, 6H), 7.00–8.00(m, 10H), 8.4–8.8(m, 2H). |

-continued

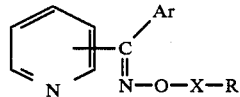

| Compound No. | Pyridine | Ar | —X—R | Physical properties | NMR (CDCl₃)δ: |
|---|---|---|---|---|---|
| 60 | 3-pyridyl | 2,3-dimethoxyphenyl | " | " | 3.00, 3.03(t, 2H), 3.48, 3.66, 3.73, 3.79(s, 6H), 4.40, 4.43(t, 2H), 7.0–8.0(m, 10H), 8.5–8.8(m, 2H). |
| 61 | 3-pyridyl | 3,4-methylenedioxyphenyl | —CH₂CH₂—Ph | Oily | 2.97, 3.00(t, 2H), 4.38, 4.41(t, 2H), 5.90, 5.94(s, 2H), 6.7–7.9(m, 10H), 8.4–8.7(m, 2H). |
| 62 | 3-pyridyl | 2,4-dimethylphenyl | " | " | 2.03(s, 3H), 2.10(s, 1H), 2.30(s, 3H), 2.97, 3.00(t, 2H), 4.37, 4.40(t, 2H), 6.8–7.9(m, 10H), 8.4–8.7(m, 2H). |
| 63 | 3-pyridyl | 2-fluorophenyl | " | " | 3.00(t, 2H), 4.43(t, 2H), 7.0–8.0(m, 11H), 8.5–8.8(m, 2H), |
| 64 | 3-pyridyl | 2-trifluoromethylphenyl | " | " | 3.00(t, 2H), 4.43(t, 2H), 7.0–8.0(m, 11H), 8.43–8.67(m, 2H). |
| 65 | 3-pyridyl | 2-nitrophenyl | " | " | 3.00(t, 2H), 4.40(t, 2H), 7.0–8.0(m, 9H), 8.0–8.5(m, 2H), 8.5–8.8(m, 2H). |
| 66 | 3-pyridyl | 2-thienyl | " | " | 3.00, 3.18(t, 2H), 4.56, 4.63(t, 2H) 6.8–8.0(m, 10H), 8.6–8.8(m, 2H). |
| 67 | 3-pyridyl | 3-pyridyl | " | " | 3.00(t, 2H), 4.43(t, 2H), 7.0–8.0(m, 10H), 8.6–8.8(m, 2H). |

Now, the activities of the compounds of the present invention will be described with reference to Test Examples.

TEST EXAMPLE 1

Calmodulin antagonism

Calmodulin is effective to increase the activities of c-AMP phosphodiesterase (PDE) from 2 to 3 times in the presence of $Ca^{2+}$. The calmodulin antagonism was determined in terms of the inhibitory activity against the 5′-AMP forming rate by adding a compound of the present invention to a reaction system comprising 50 m units of bovine cerebral calmodulin, 0.1 mM of $Ca^{2+}$, 1 μM of c-AMP ($^3$H-c-AMP 50 n Ci) and 0.875 m units of bovine myocardial c-AMP-PDE. The formed amount of 5′-AMP was measured in accordance with the Tompson et al's method (Biochemistry 10(2), 311, (1971)). As a control drug, W-7 [N-(6-aminohexyl)-5-chloro-1-naphthalenesulfonamide] was used. The results are shown in Table 1.

TABLE 1

| Compound No. | Calmodulin antagonism $IC_{50}(\mu M)$ |
| --- | --- |
| 1 | 3.8 |
| 14 | 8.0 |
| 26 | 10 |
| 43 | 4.1 |
| 46 | 8.8 |
| 47 | 6.3 |
| 57 | 9.5 |
| 58 | 3.5 |
| 62 | 8.0 |
| 63 | 5.0 |
| 64 | 6.5 |
| W-7 | 28 |

TEXT EXAMPLE 2

Calcium channel antagonism

The cecum string of a male Hartley guinea pig having a body weight of 350 g was taken out, and while air was supplied,.it was hanged with a load of 0.5 g in a high potassium Krebs solution bath (32° C) having calcium removed. Calcium chloride was accumulatively added, and the reaction was recorded by means of an isotonic tranduser (manufactured by Nippon Koden K. K.) to obtain a constant standard concentration reaction curve.

On the other hand, pretreatment with a compound of the present invention was conducted for 30 minutes, and then calcium chloride was added to the reaction bath, and from concetration reaction curve thereby obtained, $pA_2$ was obtained. The results are shown in Table 2.

TABLE 2

| Compound No. | $Ca^{2+}$ Channel antagonism $(pA_2)$ |
| --- | --- |
| 1 | 6.56 |
| 13 | 6.83 |
| 14 | 6.36 |
| 20 | 6.28 |
| 26 | 6.63 |
| 43 | 6.32 |
| 57 | 6.26 |
| 58 | 6.48 |
| 62 | 6.03 |
| 63 | 6.22 |
| 64 | 6.06 |
| 65 | 6.16 |
| 66 | 6.28 |

TEST EXAMPLE 3

Activity to improve the deformation of erythrocytes

A suspension of washed erythrocytes was prepared from a blood collected by heart puncture from a male New Zealand rabbit having a body weight of about 3 kg and having Heparin added thereto, by using a Krebs-Henseleit solution containing 20 mM of HEPES. The activity of a compound of the present invention to improve the deformation of erythrocytes was examined by measuring the time for erythrocytes to pass through a millipore filter (5 μm) by treating the suspension with $Ca^{2+}$ and with $Ca^{2+}$ ionofore A-23187 (Calimycin) in accordance with a Reid et al's method (J. Clin. Pathol. 29, 855, (1976)). As a control drug, W-7 was used. Results are shown in Table 3.

TABLE 3

| Compound No. | Activity to improve the deformation of erythrocytes [pass through time (sec.)] |
| --- | --- |
| 1 | 12 |
| 13 | 16 |
| 14 | 15 |
| 20 | 20 |
| 26 | 18 |
| 43 | 14 |
| 46 | 18 |
| 47 | 15 |
| 57 | 20 |
| 58 | 12 |
| 62 | 18 |
| 63 | 18 |
| 64 | 16 |
| 65 | 18 |
| 66 | 17 |
| W-7 | 25 |
| Calcium salt of A 23187 | 39 |

TEST EXAMPLE 4

Toxicity test

For the determination of the acute toxicity, 10 male mice having body weights of from 22 to 25 g were used as a group, and a compound in an amount corresponding to the body weight was orally administered. $LD_{50}$ was calculated by an area method from the mortality after 72 hours.

$LD_{50}$ of compounds of the present invention obtained in the Examples was more than 500 mg/kg.

FORMULATION EXAMPLE 1

Preparation of tablets

By using the following components, tablets can be prepared in accordance with a conventional method.

| | |
| --- | --- |
| Active component: O-(2-phenylethyl)-phenyl-3-pyridylethoxime | 50 mg |
| Lactose | 150 mg |
| Crystalline cellulose | 100 mg |
| Magnesium stearate | 3 mg |

As described in the foregoing, the present invention presents novel pyridylketoxime ether compounds having a calmodulin antagonism, and a pharmaceutical composition containing such a compound.

We claim:

1. A pyridylketoxime ether compound of the formula (I):

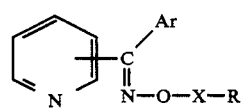

wherein Ar is a phenyl, naphthyl, furyl, thienyl, pyridyl or 1,3-dioxaindanyl group unsubstituted or substituted by a $C_1$-$C_8$ alkyl group, a $C_1$-$C_8$ alkylamino group, a $C_1$-$C_8$ alkoxy group, a $C_1$-$C_8$ alkoxycarbonyl group, a trifluoromethyl group, a nitro group or a halogen atom; X is a —$(CH_2)_m$— group wherein m is an integer of from 1 to 5, a —$(CH_2)_m$—Y— group wherein Y is an oxygen or sulfur atom and m is as defined above, or a —$CH_2$—$(CH=CH)_n$— group wherein n is an integer of 1 or 2; and R is a phenyl, naphthyl, $C_3$-$C_8$ cycloalkyl, furyl, thienyl, pyridyl or 1,3-dioxaindanyl group unsubstituted or substituted by a $C_1$-$C_8$ alkyl group, a $C_1$-$C_8$ alkylamino group, a $C_1$-$C_8$ alkoxy group, a $C_1$-$C_8$ alkoxycarbonyl group, a trifluoromethyl group, nitro group or a halogen atom, or a salt thereof.

2. The compound according to claim 1, wherein Ar is a phenyl, naphthyl, furyl, thienyl, pyridyl or 1,3-dioxaindanyl group unsubstituted or substituted by a $C_1$-$C_8$ alkyl group, a $C_1$-$C_8$ alkoxy group, a trifluoromethyl group, a nitro group or a halogen atom; X is a —$(CH_2)_m$— group wherein m is an integer of from 1 to 3, a —$(CH_2)_m$—Y— group wherein Y is an oxygen or sulfur atom and m is as defined above, a —$CH_2$—$(CH=CH)_n$— group wherein n is an integer of 1 or 2; and R is a phenyl, naphthyl $C_3$-$C_8$ cycloalkyl, furyl, thienyl, pyridyl or 1,3-dioxaindanyl group unsubstituted or substituted by a $C_1$-$C_8$ alkyl group, a $C_1$-$C_8$ alkoxy group, a trifluoromethyl group, nitro group, or halogen atom, or a salt thereof.

3. The compound according to claim 1, which is O-(2-phenylethyl)-phenyl-3-pyridylketoxime.

4. The compound according to claim 1, which is O-(2-phenylethyl)-2-chlorophenyl-3-pyridylketoxime.

5. The compound according to claim 1, wherein said $C_3$-$C_8$ cycloalkyl group for moiety R is selected from the group consisting of cyclopropyl, cyclobutyl, cyclopentyl, cyclohexyl, cycloheptyl and cyclooctyl.

6. A pharmaceutical composition for the treatment of ischemic diseases and diseases related thereto, comprising an effective amount of the pyridylketoxime ether compound or salt thereof as defined in claim 1, and a pharmaceutical carrier or diluent.

* * * * *